United States Patent
Karpe (12) 
(10) Patent No.: US 6,218,524 B1
(45) Date of Patent: Apr. 17, 2001

(54) GENETIC POLYMORPHISMS IN THE MICROSOMAL TRIGLYCERIDE TRANSFER PROTEIN PROMOTER AND USES THEREOF

(75) Inventor: Fredrik Karpe, Stockholm (SE)

(73) Assignee: Eurona Medical AB, Uppsala (SE)

( * ) Notice: Subject to any disclaimer, the term of this patent is extended or adjusted under 35 U.S.C. 154(b) by 0 days.

(21) Appl. No.: 09/153,555

(22) Filed: Sep. 15, 1998

Related U.S. Application Data (60) Provisional application No. 60/058,962, filed on Sep. 16, 1997.

(51) Int. Cl.[7] .......................... C07H 21/02; C07H 21/04; C12Q 1/68; C12N 15/00; C12N 15/09
(52) U.S. Cl. .................... 536/23.1; 536/24.3; 536/24.31; 435/6; 435/320.1
(58) Field of Search ................................. 536/23.1, 24.3, 536/24.31; 435/320.1, 2, 6

(56) References Cited

U.S. PATENT DOCUMENTS 5,595,872 * 1/1997 Wetterau et al. ......................... 435/6

OTHER PUBLICATIONS

Sharpe et al. Human Microsomal Triglyceride Transfer Protein Large Subunit Gene Structure. Biochemistry, vol. 33, pp. 9057–9061, Aug. 1994.*
Sharp et al., Biochemistry, 33:9057–9061, 1994.
Narcisi et al., Am. J. Hum. Gen., 57:1298–1310, 1995.
Sharp et al., Nature, 365:65–69, 1993.
Hagan et al., J. Biol. Chem., 269:28737–28744, 1994.
Karpe, et al., Arterioscler Thromb Vasc Biol. 1998; 18:756–761.
Haghpassand et al., J. Lipid. Res., 37:1468–1480, 1996.
Maxam–Gilbert, Proc. Natl. Acad. Sci. USA, 74:560, 1977.
Sanger et al., Proc. Natl. Acad. Sci. USA, 74:5463, 1977.
Sudhof et al., Cell, 48:1061–1069,1987.
Cotton, et al., Proc. Natl. Acad. Sci., USA, 85:4397, 1988.
Law et al., Br. Med. J., 308:367–373, 1988.
Miller et al., Nucl. Acids Res., 16:1215, 1988.
Saiki et al., Science, 239:487, 1988.
Anderson et al., Circulation, 83:356–362, 1991.
Atzel et al., Biochemistry, 32:10444–10450, 1993.
Tornvall et al., Circulation, 88:2180–2189, 1993.
Gordon et al., Proc. Natl. Acad. Sci. (USA), 91:7628–7632, 1994.
Guldberg et al., Nuc. Acids Res., 22:880, 1994.
Ravnik–Glavac et al., Hum. Mol. Genet., 3:801, 1994.
Leiper et al. J. Biol. Chem., 269:21951–21954, 1994.
Lin et al., J. Lipid Res., 36:1073–1081, 1995.
Gordon et al., Trends Cell Biol., 5:317–321. 1995.
Narcisi et al., Am. J. Hum. Gen., 57:1298–13, 1995.
Jamil et al., Proc. Natl. Acad. Sci. (USA), 93:11991–11995, 1996.

* cited by examiner

*Primary Examiner*—Stephanie W. Zitomer
*Assistant Examiner*—Cynthia Wilder
(74) *Attorney, Agent, or Firm*—Darby & Darby (57) ABSTRACT

The present invention provides diagnostic methods and compositions for determining a patient's predisposition towards developing cardiovascular diseases, which comprises identifying the allelic pattern of genes encoding microsomal triglyceride transfer protein (MTP) and comparing the MTP alleic pattern of said patient with the corresponding allelic patterns of humans with no clinical indicators of cardiovascular disease. The invention also provides isolated nucleic acids encoding MTP promoter varients, including probes and methods for using the isolated nucleic acids for detecting these polymorphisms in individuals.

7 Claims, 2 Drawing Sheets

FIG. 1

| | | |
|---|---|---|
| 1 | GCTCCAACC | |
| 10 | TCATACAGTTTCACACATAAGGACA | |
| 35 | ATCATCTATGTTTCATGAAAGTTCT | |
| 60 | ATCTACTTTAACATTATTTTGAAGT | |
| 85 | GATTGGT<u>G</u>GTGGTATGAATTAACAG | 92(G/T) |
| 110 | TTTAAATTTAAATCCTAAAATTCAG | |
| 135 | TGTGAATTTTTTATAATAGCATAAA | |
| 160 | AATTCAAAGATGTCC<u>A</u>TACAAGAAA | 175(A/G) |
| 185 | <u>A</u>ATTAAAATTTGG<u>T</u>TAGGTTTAGCA | 185(A/T) and 197(A/G) |

GENETIC POLYMORPHISMS IN THE MICROSOMAL TRIGLYCERIDE TRANSFER PROTEIN PROMOTER AND USES THEREOF

CROSS-REFERENCE TO RELATED APPLICATIONS

This application claims priority under 35 U.S.C. 119 based upon Provisional Application Ser. No. 60/058,962 filed Sep. 16, 1997, the entire disclosure of which is hereby incorporated by reference.

FIELD OF THE INVENTION

The present invention relates to allelic polymorphisms in the gene encoding microsomal triglyceride transfer protein (MTP). The invention further relates to the determination of MTP allelic patterns in an individual (i) to evaluate the individual's predisposition to cardiovascular disease; and (ii) in individuals in need of treatment, to determine the most appropriate therapeutic regimen that will result in a positive treatment outcome.

BACKGROUND OF THE INVENTION

Elevated serum cholesterol, particularly in the form of low density lipoprotein (LDL)-cholesterol, is a principal risk factor for cardiovascular disease. The protein component of LDL, apolipoprotein B (ApoB), is secreted from the liver, and the relative efficiency of apoB secretion is an important determinant of the plasma level of LDL. Microsomal triglyceride transfer protein (MTP) plays an important role in apoB secretion. Accordingly, any phenomenon that alters MTP expression or activity may influence apoB secretion and thereby affect serum LDL-cholesterol levels.

MTP is a heterodimer comprising two subunits: (i) an MTP-specific 97 kDa polypeptide and (ii) the multifunctional 55 kDa protein disulfide isomerase (PDI) (Gordon et al., *Trends Cell Biol.*, 5:317–321, 1995). MTP function is absolutely required for assembly and secretion of apoB-containing lipoproteins. Non-apoB-secreting cells can only be converted to apoB secretors if the MTP gene is provided together with the apoB gene (Gordon et al., *Proc. Natl. Acad. Sci. (USA)*, 9 1:7628–7632, 1994; Leiper et al., *J. Biol. Chem.*, 269:21951–21954, 1994). Conversely, inhibition of MTP activity in cells that normally secrete apoB results in a drastic reduction in apoB secretion (Jamil et al., *Proc. Natl. Acad. Sci. (USA)*, 9 3:11991–11995, 1996; Haghpassand et al., *J. Lipid. Res.*, 3 7:1468–1480, 1996). A complete lack of MTP activity, such as, e.g., in cells containing mutations in the MTP coding region, leads to abetalipoproteinemia (Sharp et al., *Nature*, 365:65–69, 1993; Shoulders et al., *Hum. Mol. Gen.*, 2:2109–2116, 1993; Narcisi et al., *Am. J. Hum. Gen.*, 5 7:1298–13, 1995).

The promoter region of the MTP gene is highly conserved across mammalian species and contains potential control sequences for regulating MTP expression in different cell types and in response to metabolic regulators. Transcriptional activation of the human MTP promoter is suppressed by insulin and enhanced by cholesterol (Haoan et al., *J. Biol. Chem.*, 269:28737–28744, 1994). The insulin response has also been demonstrated in HepG2 human liver carcinoma cells (Lin et al., *J. Lipid Res.*, 3 6:1073–1081, 1995). It has also been shown that liver cells in hamsters fed either a high-fat or a cholesterol-enriched diet contain higher concentrations of MTP mRNA.

The high morbidity and mortality associated with cardiovascular disease means that there is a need for methods and compositions that allow the identification of individuals who are at higher or lower risk for developing cardiovascular disease. There is also a need for methods and compositions that allow the identification of treatment regimens that result in the most positive therapeutic outcome.

SUMMARY OF THE INVENTION

The present invention provides methods and compositions that allow the predictive assessment of an individual's predisposition to developing cardiovascular disease. The methods are carried out by determining the allelic pattern of polymorphisms in the gene encoding microsomal triglyceride transfer protein (MTP). The MTP gene for use in this invention includes promoter sequences, intron sequences, protein-coding sequences, and 5'- and 3'-untranslated sequences.

Figure 1:
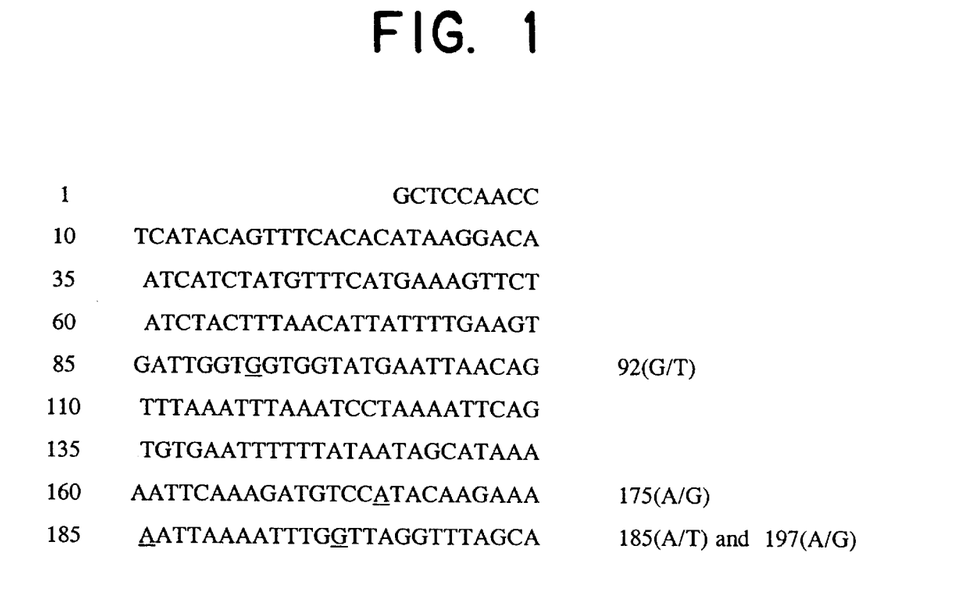
FIG. 1 shows the sequence of the human MTP promoter (SEQ ID NO. 1).

In one embodiment, the MTP promoter sequence at position 92 of the sequence depicted in FIG. 1 is evaluated, and the presence of a G or T residue at this position is determined. Non-limiting examples of other polymorphisms useful in practicing the invention include those at positions 175 (A/G); 185 (A/T); and 197 (A/G) of the sequence depicted in FIG. 1.

The present invention provides isolated nucleic acids comprising the sequence depicted in FIG. 1 SEQ. ID. NO. 1, wherein the sequence comprises one or more of the following nucleotides: a T residue at position 92; a G residue at position 175; a T residue at position 185; and a G residue at position 197. The nucleic acids include without limitation DNA or RNA, and may be used, e.g., as probes for determination of MTP allelic patterns.

The invention encompasses diagnostic methods for determining predisposition to cardiovascular disease in a patient, comprising (i) identifying the allelic pattern of genes encoding microsomal triglyceride transfer protein (MTP) in the patient;

(ii) comparing the MTP allelic pattern of the patient with the corresponding allelic patterns of healthy humans and those with one or more clinical indicators of present or future cardiovascular disease; and (iii) determining which of said corresponding allelic patterns is most similar to the allelic pattern of the patient, wherein if the MTP allelic pattern of the patient is most similar to the corresponding allelic pattern of humans with clinical indicators of cardiovascular disease, the patient has a predisposition to develop cardiovascular disease. The invention also encompasses establishing a statistically significant correlation between MTP allelic patterns and the presence or absence of one or more clinical indicators of present or future cardiovascular disease.

DETAILED DESCRIPTION OF THE INVENTION

All patents, patent applications, publications and other materials cited herein are hereby incorporated by reference in their entirety. In the case of inconsistencies, the present description, including definitions, is intended to control.

Definitions

1. Microsomal triglyceride transfer protein (MTP) catalyzes the transport of triglyceride, cholesterol ester, and phospholipid between phospholipid surfaces. Sequences comprising the gene encoding the 97 kDa subunit of MTP are deposited in GENBANK under accession numbers S71339, S74103, HSMTP, HSMTTP, S74104, and HSMTPE1-18. Sequences comprising the gene encoding the 55 kDa protein disulfide isomerase (PDI) subunit are deposited in GENBANK under accession numbers S37207, E03087, HUMPROD01, HSP2SISOM, HSU19948, E06719, and HUMPROD04.

2. "Allele" as used herein denotes an alternative version of a gene that contains one or more differences in its nucleotide sequence relative to another version of the same gene. An individual "homozygous" for a particular allele is one in which both copies of the gene contain the same allele. An individual "heterozygous" for a particular allele is one in which the two copies of the gene comprise different alleles.

3. "Allelic polymorphism" as used herein denotes a variation in the nucleotide sequence within a gene, wherein different individuals in the general population may express different variants of the gene; "allelic patterns" are combinations of allelic polymorphisms in one or several genes in a given individual.

4. "Clinical indicators of present or future cardiovascular disease" as used herein encompasses all physiological and/or molecular indicators that are associated with the diagnosis or prognosis of cardiovascular disease.

5. "Amplification" of DNA as used herein denotes the use of polymerase chain reaction (PCR) to increase the concentration of a particular DNA sequence within a mixture of DNA sequences. For a description of PCR see Saiki et al., 1988, *Science,* 239:487.

6. "Chemical sequencing" of DNA denotes methods such as that of Maxam and Gilbert (Maxam-Gilbert sequencing, Maxam and Gilbert, 1977, *Proc. Natl. Acad. Sci. USA,* 74:560), in which DNA is randomly cleaved using individual base-specific reactions.

7. "Enzymatic sequencing" of DNA denotes methods such as that of Sanger (Sanger et al., 1977, *Proc. Natl. Acad. Sci. USA,* 74:5463), in which a single-stranded DNA is copied and randomly terminated using DNA polymerase, including variations thereof well-known in the art.

8. The term "single-strand conformational polymorphism analysis" (SSCP) refers to a method for detecting sequence differences between two DNAs, comprising hybridization of the two species with subsequent mismatch detection by gel electrophoresis. (Ravnik-Glavac et al., *Hum. Mol. Genet.,* 3:801, 1994.)

9. "HOT cleavage" is defined herein as a method for detecting sequence differences between two DNAs, comprising hybridization of the two species with subsequent mismatch detection by chemical cleavage (Cotton, et al., *Proc. Natl. Acad. Sci., USA,* 85:4397, 1988).

10. "Denaturing gradient gel electrophoresis" (DDGE) refers to a method for resolving two DNA fragments of identical length on the basis of sequence differences as small as a single base pair change, using electrophoresis through a gel containing varying concentrations of denaturant (Guldberg et al., *Nuc. Acids Res.,* 22:880, 1994.)

11. As used herein, "sequence-specific oligonucleotides" refers to related sets of oligonucleotides that can be used to detect allelic variations or mutations in the prostanoid receptor genes.

12. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

13. An "isolated" nucleic acid or polypeptide as used herein refers to a nucleic acid or polypeptide that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

14. A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

15. A "probe" refers to a nucleic acid or oligonucleotide that forms a hybrid structure with a sequence in a target region due to complementarity of at least one sequence in the probe with a sequence in the target protein.

16. Nucleic acids are "hybridizable" to each other when at least one strand of nucleic acid can anneal to another nucleic acid strand under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

17. A "sample" as used herein refers to a biological sample, such as, for example, tissue or fluid isolated from an individual (including without limitation plasma, serum, cerebrospinal fluid, lymph, tears, saliva, milk, pus, and tissue exudates and sections) or from in vitro cell culture constituents, as well as samples obtained from the environment or laboratory procedures.

18. An MTP gene or cDNA corresponding to a particular sequence is understood to include alterations in the particular sequence that do not change the inherent properties of the sequence. It will be understood that additional nucleotides may be added to the 5' or 3' termini of MTP genes as part of routine recombinant DNA manipulations. Furthermore, sequence-conservative DNA substitutions, i.e., changes in the sequence of the protein-coding region that do not change the encoded amino acid sequence, may also be accommodated.

19. An "immunogenic component" as used herein refers to a protein, peptide, or chemical entity which can elicit the production of specific antibodies, i.e., antibodies which bind with high affinity to the specific protein, peptide, or chemical entity.

20. "Therapeutic regimen", as used herein, refers without limitation to methods for the elimination or amelioration of symptoms and events associated cardiovascular disease. Such methods include, without limitation, alteration in diet, lifestyle, and exercise regimen; invasive and noninvasive surgical techniques such as atherectomy, angioplasty, and coronary bypass surgery; and pharmaceutical interventions, such as administration of ACE inhibitors, angiotensin II receptor antagonists, diuretics, alpha-adrenoreceptor antagonists, cardiac glycosides, phosphodiesterase inhibitors, beta-adrenoreceptor antagonists, calcium channel blockers, HMG-CoA reductase inhibitors, and organic nitrites. Intervention with pharmaceutical agents not yet known whose activity correlates with particular allelic patterns associated with cardiovascular disease also falls under the present definition of "therapeutic regimen".

21. "Most positive treatment outcome" as used herein refers to the result of the administration or application of a treatment regimen which most effectively ameliorates, eliminates, or prevents occurrence of cardiovascular disease, with the fewest and least severe side effects.

The present inventors have surprisingly and unexpectedly discovered the existence and nature of genetic polymorphisms within the promoter region of the human microsomal triglyceride transfer protein (MTP). They have further discovered a direct correlation between particular MTP promoter polymorphisms, serum concentrations of LDL-cholesterol and the risk for cardiovascular disease. Thus, the allelic pattern of MTP promoter sequences in an individual can serve as an indicator of predisposition to various forms of cardiovascular disease. The present invention provides isolated nucleic acids encoding MTP promoter variants, including probes; and methods for using the isolated nucleic acids for detecting these polymorphisms in individuals within the general population. Similarly, polymorphisms within the MTP protein-coding sequence are also predicted to correlate with differences in plasma LDL-cholesterol and thereby also serve as indicators of predisposition to cardiovascular disease. Also encompassed by the invention are methods for determining a subject's predisposition to cardiovascular disease that involve determining the subject's MTP promoter allelic pattern and/or MTP coding sequence allelic pattern.

MTP promoter sequence polymorphisms

Several polymorphic sequences have been identified within the MTP promoter sequence. The previously identified MTP promoter sequence, and the indicated polymorphic sequences, are shown in FIG. 1.

Briefly, MTP promoter sequences were determined in twenty randomly selected healthy Caucasian males aged 30–45 years. Polymerase chain reaction (PCR) was used to amplify the MTP promoter region and the amplified DNA was sequenced (see, e.g., Example 1 below). One common polymorphism (a G->T substitution) is located at position 92 upstream from the MTP transcriptional start site. A second common polymorphism (an A->T substitution) is located at position 185. Less common polymorphisms were also identified at positions 175(A->G) and 388(A->G).

The frequency of these allelic polymorphisms was further assessed in 184 Swedish men. The frequency of the MTP-92 G/T polymorphism was 0.75/0.25 and the frequency of the MTP 185 A/T polymorphism was 0.68/0.32. Table 1 shows the distribution of MTP promoter allelic patterns in this population.

TABLE 1

| MTP Allelic Patterns | | |
|---|---|---|
| 92 | 185 | Number |
| G/G | A/A | 84 |
| G/T | A/A | 4 |
| T/T | A/A | — |
| G/G | A/T | 17 |
| G/T | A/T | 58 |
| T/T | A/T | — |
| G/G | T/T | 2 |
| G/T | T/T | 8 |
| T/T | T/T | 11 |
| All | | 184 |

The functional significance of these polymorphisms was investigated by testing the ability of polymorphic MTP promoter sequences to (i) interact with transcription factors in vitro and (ii) stimulate transcription in intact cells. These experiments are described in detail in Example 2 below. Briefly, electromobility shift assays demonstrated that the 92 G variant binds additional nuclear proteins as compared with the 493 T variant. Furthermore, when tandem copies of a minimal promoter sequence encompassing the 92 polymorphism were coupled to the chloramphenicol acetyl transferase (CAT) gene and expressed in HepG2 cells, the 92 T variant exhibited almost twice the level of transcriptional activity as the 92 G variant.

In human subjects, there is a direct correlation between MTP promoter allelic pattern and plasma lipoprotein concentrations (see, e.g., Example 3 below). Subjects homozygous for the 92 T allele had significantly lower plasma LDL-cholesterol, total cholesterol, and triglyceride levels as compared with subjects homozygous for the 92 G allele and heterozygotes. Thus, according to the invention, determination of an individual's MTP promoter allelic pattern can indicate his/her predisposition to developing cardiovascular disease.

The present invention provides isolated nucleic acids comprising MTP promoter allelic polymorphisms, wherein the sequences comprise one or more of the following residues: a T residue at position 92; a G residue at position 175; a T residue at position 185; and a G residue at position 197. In certain embodiments, the invention encompasses isolated nucleic acid fragments comprising all or part of the MTP promoter variant sequences disclosed herein. The fragments are at least about 8 nucleotides in length, preferably at least about 12 nucleotides in length, and most preferably at least about 15–20 nucleotides in length.

Also encompassed by the invention are nucleic acids that are hybridizable to, or derived from, the MTP promoter allelic variants described above. In one embodiment, the invention relates to isolated nucleic acids capable of hybridizing with the allelic variant sequences or with their complements under the hybridization conditions defined below.

Prehybridization treatment of the support (nitrocellulose filter or nylon membrane), to which is bound the nucleic acid capable of hybridizing with that of an MTP promoter allelic variant, at 65° C. for 6 hours with a solution having the following composition: 4×SSC, 10×Denhardt (1×Denhardt is 1% Ficoll, 1% polyvinylpyrrolidone, 1% BSA (bovine serum albumin); 1×SSC consists of 0.15 M of NaCl and 0.015 M of sodium citrate, pH 7);

Replacement of the pre-hybridization solution in contact with the support by a buffer solution having the following composition: 4×SSC, 1×Denhardt, 25 mM NaPO4, pH 7, 2 mM EDTA, 0.5% SDS, 100 mu g/ml of sonicated salmon sperm DNA containing a nucleic acid derived from the sequence of an MTP promoter allelic variant as probe, in particular as radioactive probe, and previously denatured by a treatment at 100° C. for 3 minutes;

Incubation for 12 hours at 65° C.;

Successive washings with the following solutions: (i) four washings with 2×SSC, 1×Denhardt, 0.5% SDS for 45 minutes at 65° C.; (ii) two washings with 0.2×SSC, 0.1×SSC for 45 minutes at 65° C.; and (iii) 0.1×SSC, 0.1% SDS for 45 minutes at 65° C.

The invention also encompasses any nucleic acid exhibiting the property of hybridizing specifically with MTP promoter allelic variants under the conditions described above, but at 40° C., including successive washings in 2×SSC at 45° C. for 15 minutes.

It will be understood that the conditions of hybridization defined above constitute preferred conditions for the hybridization, but are in no way limiting and may be modified without in any way affecting the properties of recognition and hybridization of the probes and nucleic acids mentioned above.

The salt conditions and temperature during the hybridization and the washing of the membranes can be modified in the sense of a greater or lesser stringency without the detection of the hybridization being affected. For example, it is possible to add formamide in order to lower the temperature during hybridization.

Also encompassed by the invention are isolated nucleic acids comprising sequences that correspond to allelic variants in the MTP protein-coding sequence. In preferred embodiments, these allelic variants, whether homozygous or heterozygous, correlate with alterations in plasma LDL-cholesterol in individuals carrying the variants relative to individuals containing wild-type MTP-encoding sequences.

DNA, VECTORS, and HOST CELLS

In practicing the present invention, many conventional techniques in molecular biology, microbiology, and recombinant DNA, are used. Such techniques are well known and are explained fully in, for example, Sambrook et al., 1989, *Molecular Cloning: A Laboratory Manual,* Second Edition, Cold Spring Harbor Laboratory Press, Cold Spring Harbor, N.Y.; *DNA Cloning: A Practical Approach,* Volumes I and II, 1985 (D. N. Glover ed.); *Oligonucleotide Synthesis,* 1984, (M. L. Gait ed.); *Nucleic Acid Hybridization,* 1985, (Hames and Higgins); *Transcription and Translation,* 1984 (Hames and Higgins eds.); *Animal Cell Culture,* 1986 (R. I. Freshney ed.); *Immobilized Cells and Enzymes,* 1986 (IRL Press); Perbal, 1984, *A Practical Guide to Molecular Cloning;* the series, *Methods in Enzymology* (Academic Press, Inc.); *Gene Transfer Vectors for Mammalian Cells,* 1987 (J. H. Miller and M. P. Calos eds., Cold Spring Harbor Laboratory); and *Methods in Enzymology* Vol. 154 and Vol. 155 (Wu and Grossman, and Wu, eds., respectively).

Insertion of nucleic acids (typically DNAs) comprising the sequences of the present invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by native MTP sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed MTP-derived sequences or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression. Non-limiting examples of suitable vectors include without limitation pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Recombinant cloning vectors will often include one or more replication systems for cloning or expression, one or more markers for selection in the host, e.g. antibiotic resistance, and one or more expression cassettes. The inserted MTP-derived sequences may be synthesized by standard methods, isolated from natural sources, or prepared as hybrids, etc. Ligation of the MTP sequences to transcriptional regulatory elements and/or to other amino acid coding sequences may be achieved by known methods. Suitable host cells may be transformed/transfected/infected as appropriate by any suitable method including electroporation, CaCl$_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *S. aureus, E. coli, B. Subtilis, Saccharomyces cerevisiae, Saccharomyces carlsbergensis, Schizosaccharomyces pombi*, SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced MTP-derived peptides and polypeptides.

Advantageously, vectors may also include a transcription regulatory element (i.e., a promoter) operably linked to the MTP-derived portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; araBAD (arabinose) operon promoter; lambda-derived P$_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and polyA addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are well described in the art.

Nucleic acids encoding wild-type or variant MTP-derived sequences may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use as probes for the detection of genetic polymorphisms and as templates for the recombinant production of normal or variant MTP-derived peptides or polypeptides.

Probes in accordance with the present invention comprise without limitation isolated nucleic acids of about 10–100 bp, preferably 15–75 bp and most preferably 17–25 bp in length, which hybridize at high stringency to one or more of the MTP gene-derived polymorphic sequences disclosed herein or to a sequence immediately adjacent to a polymorphic position. Furthermore, in some embodiments a full-length gene sequences may be used as a probe. In one series of embodiment, the probes span the polymorphic positions in the MTP genes disclosed above. In another series of embodiments, the probes correspond to sequences immediately adjacent to the polymorphic positions.

APPLICATIONS

The present invention provides diagnostic methods for screening patient populations to identify those individuals at risk for developing cardiovascular disease and to determine the most appropriate therapeutic regimen for an individual with a given allelic pattern, i.e., the therapeutic regimen that will result in the most positive treatment outcome. The methods involve identification of the allelic patterns of MTP genes (including promoter and protein-coding sequences) in an individual. The methods involve testing blood cells or DNA from individual patients for the presence of alternate MTP alleles, so as to identify a characteristic allelic pattern or genotype. In general, an individual's MTP allelic pattern is compared with the distribution of allelic patterns in different test populations. Depending upon which receptors are being analyzed, this screening can serve a variety of different diagnostic uses.

In practicing the present invention, the presence of different MTP alleles in an individual patient is determined by either: 1) molecular detection of MTP promoter DNA variants, or of DNA or RNA encoding MTP variants, using nucleic acid probes, with or without nucleic acid sequencing ("genotypic characterization") or 2) immunological detection of MTP protein variants present in MTP-expressing tissues, including without limitation liver and intestine ("phenotypic characterization").

In a first embodiment, DNA is obtained from a patient, and the presence of DNA sequences corresponding to particular MTP alleles is determined. The DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation. DNA is extracted from the cell source or body fluid using any of the numerous methods that are standard in the art. It will be understood that the particular method used to extract DNA will depend on the nature of the source. The minimum amount of DNA to be extracted for use in the present invention is about 25 pg (corresponding to about 5 cell equivalents of a genome size of $4\times10^9$ base pairs).

Once extracted, the DNA may be employed in the present invention without further manipulation. Alternatively, the DNA region corresponding to all or part of an MTP gene may be amplified by PCR. In this case, the amplified regions are specified by the choice of particular flanking sequences for use as primers. Amplification at this step provides the advantage of increasing the concentration of the DNA sequences. The length of DNA sequence that can be amplified ranges from 80 bp to up to 30 kbp (Saiki et al., 1988, Science, 239:487). Preferably, primers are used that define a relatively short segment containing sequences that differ between different allelic forms of the receptor.

The presence of MTP allele-specific DNA sequences may be determined by any known method, including without limitation direct DNA sequencing, hybridization with allele-specific oligonucleotides, allele-specific PCR, ligase-PCR, HOT cleavage, denaturing gradient gel electrophoresis (DDGE), and single-stranded conformational polymorphism (SSCP). Direct sequencing may be accomplished by chemical sequencing, using the Maxam-Gilbert method, or by enzymatic sequencing, using the Sanger method. In the latter case, specific oligonucleotides are synthesized using standard methods and used as primers for the dideoxynucleotide sequencing reaction.

Preferably, DNA from a patient is subjected to amplification by polymerase chain reaction (PCR) using specific amplification primers, followed by hybridization with allele-specific oligonucleotides. Alternatively, SSCP analysis of the amplified DNA regions may be used to determine the allelic pattern.

In an alternate embodiment, biopsy tissue derived from liver or intestine, or blood cells, are isolated from a patient. Antibodies that are capable of distinguishing between different allelic forms of MTP are then applied to the tissue to determine the presence and relative amount of each allelic form. The antibodies may be polyclonal or monoclonal, preferably monoclonal. Measurement of specific antibody binding to cells may be accomplished by any known method e.g. quantitative flow cytometry, or enzyme-linked or fluorescence-linked immunoassay. The presence or absence of a particular allele, as well as the allelic pattern (i.e. homozygosity vs. heterozygosity) is determined by comparing the values obtained from a patient with norms established from populations patients of known gentoypes.

In an alternate embodiment, RNA is isolated from liver or intestinal tissue, using standard methods well known to those of ordinary skill in the art such as guanidium thiocyanate-phenol-chloroform extraction (Chomocyznski et al., 1987, *Anal. Biochem.*, 162:156.) The isolated RNA is then subjected to coupled reverse transcription and amplification by polymerase chain reaction (RT-PCR), using specific oligonucleotide primers. Conditions for primer annealing are chosen to ensure specific reverse transcription and amplification; thus, the appearance of an amplification product is diagnostic of the presence of particular alleles. In another embodiment, RNA encoding MTP is reverse-transcribed and amplified, after which the amplified sequences are identified by hybridization to allele-specific oligonucleotides or by direct sequencing.

The present invention also encompasses the identification and analysis of new alleles of MTP genes that may be associated with differences in, e.g., LDL-cholesterol levels and/or cardiovascular disease. In this embodiment, genomic DNA may be amplified, or, alternatively, RNA encoding MTP may be selectively reverse-transcribed and amplified as described above. The DNA product is then sequenced directly, and the sequence compared with the sequence of the known alleles of the gene of interest. Once a new allele has been identified, allele-specific DNA primers and/or allele-specific antibodies can be prepared by standard methods. These reagents can then be used for screening of individuals for MTP alleles as described above. In practicing the present invention, the distribution of MTP allelic patterns in a large number of individuals exhibiting particular clinical signs is determined by any of the methods described above, and compared with the distribution of MTP allelic patterns in patients that have been matched for age and ethnic origin who exhibit a different set of clinical signs. A statistical method such as a 2×3 Chi square test is then used to determine whether the allele frequencies in the groups are the same or different. In this manner, it is possible to establish statistically significant correlations between a given physiological status (including, e.g., serum lipoprotein levels or efficacy of a particular treatment regimen) and previously known or novel MTP allelic patterns. It is contemplated that correlations between particular MTP allelic patterns and particular cardiovascular diseases or symptoms will provide an important prognosticator of predisposition to disease and/or responsivity to particular treatment regimen.

Diagnostic Methods and Kits

The present invention provides kits for the determination of the sequence at polymorphic positions within the MTP gene in an individual. The kits comprise a means for determining the sequence at one or more polymorphic positions, and may optionally include data for analysis of polymorphic patterns. The means for sequence determination may comprise suitable nucleic acid-based. Preferably, the kits also comprise suitable buffers, control reagents where appropriate, and directions for determining the sequence at a polymorphic positions. The kits may also comprise data for correlation of particular polymorphic patterns with desirable treatment regimens or other indicators.

Nucleic-acid based diagnostic methods and kits

The invention provides nucleic acid-based methods for detecting polymorphic patterns in a biological sample. The sequence at particular polymorphic positions in the promoter for the gene encoding MTP is determined using any suitable means known in the art, including without limitation hybridization with polymorphism-specific probes and direct sequencing.

The present invention also provides kits suitable for nucleic acid-based diagnostic applications. In one embodiment, diagnostic kits include the following components:

(i) Probe DNA: The probe DNA may be pre-labelled; alternatively, the probe DNA may be unlabelled and the ingredients for labelling may be included in the kit in separate container; and (ii) Hybridization reagents: The kit may also contain other suitably packaged reagents and materials needed for the particular hybridization protocol, including solid-phase matrices, if applicable, and standards.

In another embodiment, diagnostic kits include:

(i) Sequence determination primers: Sequencing primers may be prelabelled or may contain an affinity purification or attachment moiety; and (ii) Sequence determination reagents: The kit may also contain other suitably packaged reagents and materials needed for the particular sequencing protocol. In one preferred embodiment, the kit comprises a panel of sequencing primers, whose sequences correspond to sequences adjacent to the following polymorphic positions in the MPT promoter: 92, 175, 185 and 197, as well as a means for detecting the presence of each polymorphic sequence.

The following are intended as non-limiting examples of the invention.

EXAMPLE 1: Isolation and Dermination of the Nucleic Acids Encoding Polymorphic Variants of the MTP Gene The following experiments were performed to identify polymorphic variants of the MTP gene promoter sequence.

I. Methods:

Human subjects: A total of 184 healthy Caucasian men, aged 30–45 years were recruited at random from a register containing all permanent residents in the Stockholm Metropolitan area (response rate 70%). Men with documented coronary heart disease or any other chronic disease were excluded. The mean age of the study group was 40.3±3.4 years, and the body mass index was 24.5±2.8 kg/m².

Blood sampling, DNA procedures and lipoprotein analyses: Blood sampling, preparation of plasma and quantification of major fasting plasma lipoproteins were as described (Tornvall et al., Circulation, 8 8:2180–2189 1993). For DNA procedures, nucleated cells from frozen whole blood were prepared according to Sambrook et al., and DNA was extracted by a salting-out method (Sambrook et al., *A Laboratory Manual,* 1989). All subjects were also genotyped for the apoE polymorphism (Miller et al., *Nucl, Acids Res.,* 16:1215, 1988).

Gene sequencing: DNA for direct sequencing of the MTP promoter was amplified in a two-step nested PCR reaction. About 100 ng of genomic DNA was used for each individual PCR reaction. Primers were designed based on the published promoter sequence (−743 base pairs in the 5'-direction) (Sharp et al., *Nature,* 365:65–69, 1993). First, a round of PCR was performed using the following primers: 5'-CCCTCTTAATCTCTTTCCTAGAA-3' (designated MTP-1) SEQ ID NO:2 and 5'-AAGAATCATTGACCAGCAATC-3' (designated MTP-2) SEQ ID NO:3. Then, one µl of this PCR reaction was used for a second PCR reaction, utilizing one unlabeled and one biotin-labeled primer at a concentration of 0.1 µM each. These primers were MTP-1 and 5'-CCAGCTAGGAGTCACTGAGA-3' (biotinylated) SEQ ID NO:4. All amplifications were performed for thirty cycles at 96° C. for 1 min, 60° C. for 30 s, and 72° C. for 90 s in a buffer containing 1.0 mM $MgCl_2$, 0.2 mM dNTP, 10 mM Tris-HCl, pH 8.4 at 70° C., 0.1% Tween 20, and 0.2 U Taq polymerase. The biotinylated PCR fragments were immobilized by binding to streptavidin-coated magnetic beads (Dynabeads, Dynal, Oslo, Norway), and the non-biotinylated strands were removed by incubation in 50 µl 0.15 M NaOH for 5 min at room temperature. The bound DNA was rinsed three times and suspended in 13 µl distilled water.

Gene sequencing was performed by the chain-termination method, using fluorescently-labeled primers distributed within the 750 bp promoter region. These were: 5'-TAGAAATGAGATTCAGAAAGGAC-3' (designated MTP-7fl) SEQ ID NO.:5, 5'-CAATCATCTATGTTTC ATCAA-3' (designated MTP-7 fl) SEQ ID NO:6 and 5'-AAGTTTCCTCATGGGTGA-3' (designated MTP-8 fl) SEQ ID NO:7. The products were analyzed using a Pharmacia A.L.F. DNA Sequencer. All primers were synthesized on a Gene Assembler Plus (Pharmacia, Sweden). Labeling of primers with biotin or fluorescein was performed by incorporating BioDite or FluorePrime phosphoamidites (Pharmacia, Sweden), respectively, during synthesis. Fluorescence-labeled primers were purified by reverse-phase chromatography on a PepRPC column (Pharmacia FPLC). Normally, the sequences could be read with a considerable overlap, thus confirming the sequence.

Genotyping: Primers MTP-1 and MTP-2 were used for genotyping of the 185 A/T polymorphism. First, a single-step PCR reaction was further optimized by increasing the $MgCl_2$ concentration to 2.0 µM and changing to 35 cycles at 94° C. for 30 s, 55° C. for 60 s, and 72° C. for 3 min. The PCR product was then incubated with the restriction enzyme Ssp-1 (4 Units). The 185T-allele gave rise to a cutting site. The restriction length polymorphism (RFLP) was inspected after agarose gel (1.5%) electrophoresis of the incubate. The 185A-allele gave rise to the full-length fragment (838 bp) whereas the 185T-allele gave rise to two shorter fragments (494 and 344 bp, respectively). The 92G/T polymorphism does not give rise to a cutting site with any common restriction enzyme. However, a base pair mutation in the 5' primer used for PCR of a gene product covering the 92 site gave rise to a Hph-1 cutting site for the 92G allele. The PCR reaction, which used the following primers: 5'-GGATTTAAATTTAAACTGTTAATTCATATCAC-3' (designated MTP1U) SEQ ID NO:8 and 5'-AGTTTCACACATAAGGACAATCATCTA-3' (designated MTP2D) SEQ ID NO:9 gave rise to a 109 bp fragment and the gene product was cleaved by Hph-1. Here, the $MgCl_2$ concentration was increased to 5 mM, and amplification comprised 35 cycles at 94° C. for 30 s, 57° C. for 60 s, and 72° C. for 2 min. The PCR product was incubated with HphI and the RFLP was studied after high-resolution 3% agarose gel electrophoresis (Metaphor-agarose). The 92T allele gave rise to a full-length fragment (109 base pairs), whereas the 92G allele gave rise to two fragments of 89 and 20 base pairs, respectively.

II. Results

Two common polymorphisms were identified in the promoter region of MTP. One was a G→T substitution at nucleotide 92, the other was an A→T substitution at nucleotide 185. Two less common polymorphisms were also found at 175 (A/G) and at 197 (A/G). The allele frequency for the MTP 92G/T polymorphism was 0.75/0.25 in the population of 184 native Swedish men. The corresponding figures for the MTP 185A/T polymorphism were 0.68/0.32. The combination of genotypes for the 92 and 185 sites within the group of 184 subjects are shown in Table 1 above.

EXAMPLE 2: Functional Differences Between MTP Promoter Allelic Variants

The following experiments were performed to compare the transcriptional activating capacity of different MTP promoter allelic variants.

I. Methods

Electrophoretic Mobility Shift Assay (EMSA): Nuclear extracts were prepared according to Alksnis et al. (Anderson et al., *Circulation,* 83:356–362, 1991). All buffers were freshly supplemented with leupeptin (0.7 µ/ml), aprotinin (16.6 µg/ml), PMSF (0.2 µM) and 2-mercaptoethanol (0.33 µl/ml). The protein concentration in the extracts was estimated by the method of Kalb and Bernlohr (Atzel et al., *Biochemistry,* 32:10444–10450, 1993). Incubation for EMSA was conducted as described (Sudhof et al., *Cell,* 48:1061–1069, 1987), and the reaction products were applied to a 7% (wt/vol) polyacrylamide gel (80:1 acrylamide/N,N'methylene—bisacrylamide weight ratio), after which electrophoresis was performed in 2.5 mM Tris/22.5 mM boric acid/0.5 mM EDTA buffer for 2.5 h at 200 V. Non-radioactive competitor DNAs (either identical, or of the opposite allelic variant, or of non-specific origin) were added.

Transfection assay: Twenty-four hours before transfection, cells were plated in DMEM supplemented with 10% newborn calf serum. Two to four hours before transfection, the dishes received fresh medium. Cells were incubated for 16 hours with calcium-phosphate precipitated DNAs (15 µg of plasmid per 90-mm dish) (Tornvall et al., *Circulation,* 88:2180–2189, 1993). After a 2-min 15% glycerol shock, fresh medium was added. Cells were harvested for assay of transient expression 36 hours later. The pSV-β-galactosidase gene (Promega) was cotransfected as an internal control.

II. Results

Figure 2:
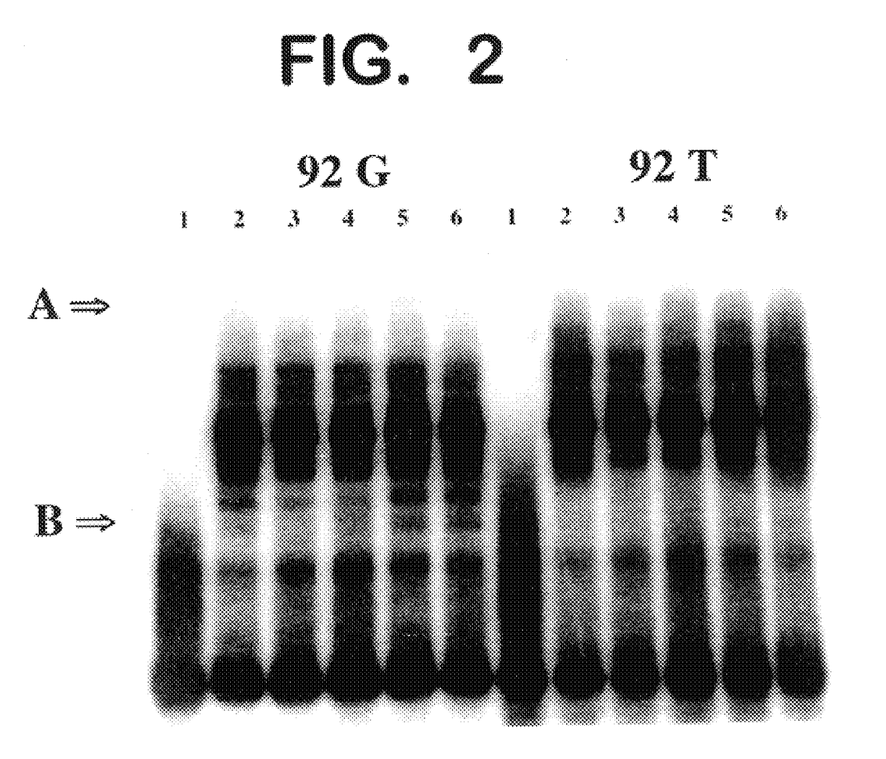
FIG. 2 is a photograph of a gel showing an Electrophoretic Mobility Shift Assay (EMSA) performed to determine whether there was differential binding of nuclear protein(s) to the polymorphic sites that may regulate the transcriptional activity of the gene.

EMSA was performed to determine whether there is differential binding of nuclear protein(s) to the polymorphic sites that might regulate the transcriptional activity of the gene. By use of labeled sequence-specific and excess of non-labeled non-specific oligonucleotides, two factors (bands on the EMSA gel) showed sequence-specific binding to the MTP92 site (FIG. 2), whereas the EMSA pattern did not differ between the MTP185 constructs. The first factor (Factor A) bound to the 92G allele. A second factor represented by a double band (Factor B) only appeared with the 92G allele. The EMSA pattern did not differ between the MPT185 constructs.

Figure 3:
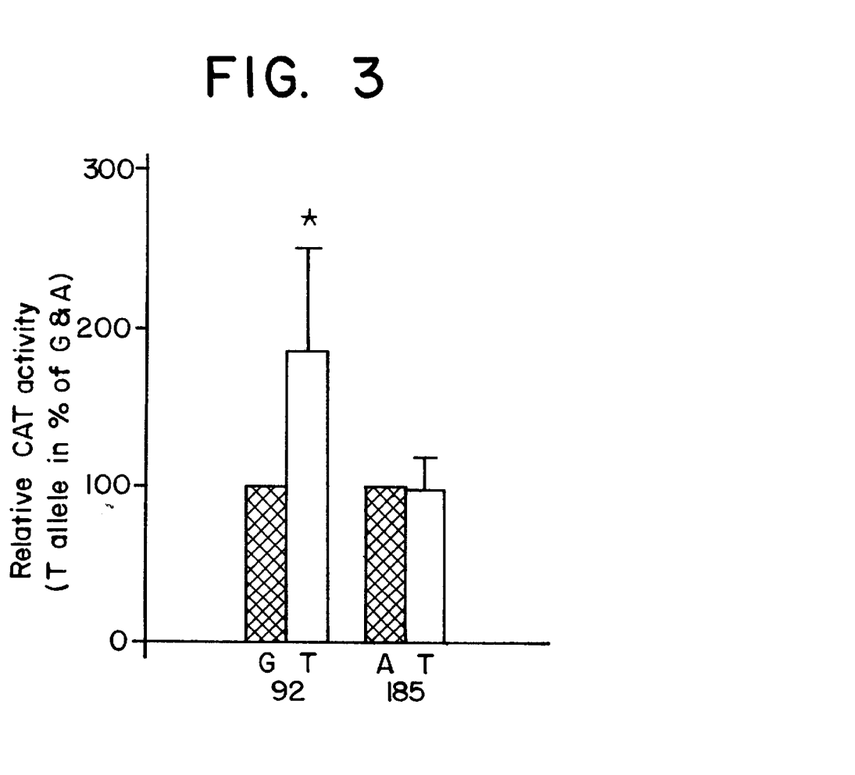
FIG. 3 is a bar graph showing the results of a transfection assay conducted to assess the allele-specific transcriptional activity of the MTP promoter.

A transfection assay was conducted to assess whether the allele-specific binding of nuclear proteins affects trascriptional activity of the MTP promoter. Two tandem copies of a 31-base pair DNA segment containing either of the 92G or T alleles were inserted upstream of a minimal and heterologous promoter driving the chloramphenicol acetyltransferase (CAT) gene. The minimal promoters were used to delineate the impact of putative transcriptional activators or repressors on the 92G/T sites. FIG. 3 shows the expression of the CAT gene in HepG2 cells. The promoter constructs harboring the 92T site exhibited an almost two-fold higher transcriptional activity compared with the 92G construct (+187±69%, p<0.05). One interpretation of this finding (together with the EMSA pattern) is that Factor A and/or B could act as transcriptional repressors.

There was no difference in transcriptional activity between constructs containing either of the two 185 A or T alleles (FIG. 3).

EXAMPLE 3: Association of MTP promoter polymorphism and plasma lipoprotein levels The following experiments were performed to investigate the physiological consequences of MTP promoter allelic polymorphisms.

I. Methods

Blood sampling, DNA procedures and lipoprotein analyses: Blood sampling, preparation of plasma and quantification of major fasting plasma lipoproteins were as described previously (Sharp et al., *Biochemistry*, 33:9057–9061, 1994). For DNA procedures, nucleated cells from frozen whole blood were prepared according to Sambrook et al. (Sambrook et al., *Molecular cloning: A Laboratory Manual*, 1989), and DNA was extracted by a salting-out method (Miller et al., *Nucl. Acids Res.*, 16:1215, 1988). DNA genotyping was performed as described in Example 1 above.

II. Results

Subjects who were homozygous for the rate 92T allele had significantly lower plasma LDL cholesterol and triglyceride levels compared with both heterozygotes (i.e., 92G/T) and homozygotes for the common allele (i.e., 92G/G (Table 2)). The plasma LDL cholesterol concentration of the 92T/T individuals was on average 22% lower than that of carriers of one or two copies of the 92G allele. Similarly, men who were homozygous for the 92T allele tended to have lower plasma total cholesterol (p=0.06 compared with individuals with either 92G/G or G/T genotypes). Otherwise, there were no differences in VLDL or HDL lipid concentrations according to the MTP-92 genotype.

TABLE 2

Plasma Concentrations of Major Lipoproteins According to MTP-92G/T Genotype

| | Plasma | | VLDL | | LDL | | HDL |
|---|---|---|---|---|---|---|---|
| | Chol. (mM) | TG (mM) | Chol. (mM) | TG (mM) | Chol. (mM) | TG (mM) | Chol. (mM) |
| 92G/G (n = 103) | 5.51 ± 0.99 | 1.35 ± 0.67 | 0.45 ± 0.28 | 0.87 ± 0.59 | 3.74 ± 0.69 | 0.32 ± 0.10 | 1.22 ± 0.31 |
| 92G/T (n = 70) | 5.53 ± 1.12 | 1.36 ± 0.86 | 0.46 ± 0.37 | 0.86 ± 0.73 | 3.70 ± 0.98 | 0.33 ± 0.12 | 1.30 ± 0.34 |
| 92T/T (n = 11) | 4.72 ± 0.74 | 1.14 ± 039 | 0.42 ± 0.24 | 0.77 ± 0.39 | 2.90 ± 0.59 | 0.23 ± 0.04 | 1.31 ± 0.41 |

III. Implications

Polymorphisms in the promoter region of MTP have not been reported previously. We have detected a common G/T polymorphism located 493 base pairs upstream from start of the transcription of the MTP gene. The rare allele, with an allele frequency of approximately 0.25, confers a significantly higher transcriptional activity. Healthy homozygotes for this genetic variant, comprising about 6% of healthy Caucasian, middle-aged Swedish men, have a low LDL cholesterol concentration in plasma.

The difference in LDL cholesterol concentration between carriers of the MTP-92G/G or G/T genotypes and carriers of the MTP-92T/T genotypes is approximately 0.8 mmol/l. The impact of homozygosity for the MTP-92T allele on cardiovascular risk is therefore likely to be of major significance. Law and colleagues calculated that a 0.6 mmol/l reduction in serum cholesterol would correspond to a 50% lowering of the risk of future ischemic heart disease in 40-year old men (Law et al., *Br. Med. J.*, 308:367–373, 1988). Using the Framingham score, the 10-year risk of developing of cardiovascular disease would be 25% lower in subjects with an MTP-92T/T genotype (Anderson et al., *Circulation*, 83:356–362, 1991). Thus, this common genetic variation of the MTP promoter is likely to have important implications for cardiovascular disease.

Genotyping for the MTP-92 polymorphism can be used for diagnostic and prognostic purposes in patients suffering from various kinds of hyperlipoproteinemias. Furthermore, MTP may play an important role in intracellular compartmentalization of cholesterol. As MTP is also involved in cholesterol transfer (Atzel et al., *Biochemistry*, 32:10444–10450, 1993), an elevated MTP activity could lead to a depletion of cholesterol from intracellular membranes. This would, in turn, be sensed by sterol-regulated binding proteins acting on the promoter of the LDL receptor gene (Sudhof et al., *Cell,* 48:1061–1069, 1987). Perturbation of the intracellular cholesterol homeostasis secondary to elevated MTP activity is likely to be sensed similarly to HMG-CoA reductase inhibition, in which up-regulation of LDL receptors is the key mechanism underlying the lowering of LDL cholesterol in plasma. In line with this reasoning, MTP activity is of importance for the outcome of dietary or pharmacological hypolipidemic treatment. If particular MTP genotypes are linked to a more or less favorable treatment outcome, genotyping would be the preferred way to tailor the treatment strategy.

EXAMPLE 4: Evaluation of Risk in Developing Myocardial Infarction (MI) Based on Variation in the MTP Gene The following experiments were performed to identify the risk of developing MI with individuals having TT in position 92 in the promoter of MTP.

I. Methods

Human Subjects: a total of 103 subjects diagnosed with myocardial infarction and 100 subjects diagnose healthy with regard ischemic heart disease were recruited from the UPPSALA Longitudinal Survey of adult men. The mean age of the study group was 73±2 years at the point of analysis.

Blood sampling and DNA procedures were performed as in Example 1 above.

The characterization of the genotype in position 92 in the MTP promoter was performed as set forth below.

PCR was performed as follows:

The fragment was amplified from genomic DNA with the two primers:

Primer 1: MTP92FT: 5'-AGT CAC GAC GTT GTA AAA CGA CGG CCA GTA CAT AAG GAC AAT CAT CTA TGT T-3'SEQ ID NO:10

Primer 2: MTP92RB: 5'-TCT TGT ATG GAC ATC TTT GAA-3'SEQ ID NO:11

The fragment was amplified from genomic DNA under the following conditions:

| | |
|---|---|
| 10x PCR buffer II (Perkin Elmer) | 5 µl |
| MgCl₂ solution 2.5 mM (Pharmacia Elmer) | 7 µl |
| Ultrapure dNTP set 2.5 mM (Pharmacia Biotech) | 2.5 µl |
| Primer 1 (3.3 µM) | 1 µl |
| Primer 2 (3.3 µM) | 1 µl |
| AmpliTaqGold ®DNA polymerase (Perkin Elmer) | 0.5 µl |
| R/O purified water q.s. | Tot. 45 µl |

The amplification was performed with the following thermal cycling (program):

| Temperature | Time | Temperature | Time | Temperature | Time | No. of Cycles |
|---|---|---|---|---|---|---|
| 95° C. | 10 min | | | | | 1 |
| 95° C. | 15 s | 48° C. | 30 s | 72° C. | 5 min | 50 |
| 22° C. | ∞ | | | | | |

DNA sequencing

All of the PCR products were subjected to solid phase sequencing according to the protocol commercially available from Pharmacia Biotech. The sequencing reactions were performed with a sequencing primer having a complementary sequence to the MTP92FT primer. The nucleotide sequence of the sequencing primer was 5'-CGACGTTGTAAAACGACGGCCAGT-3'SEQ ID NO:12, and the primer was fluorescently labeled with a Cy5.5 molecule on the 5'-nucleotide. The positions carrying a genetic variation were identified by determination of the nucleotide sequence by the use of the Micro Gene Blaster System (Visible Genetics).

TABLE 3

Probabilities for developing a myocardial infarction or not related to a specific genotype in position 92 in the promoter of the MTP gene. Three different genotypes are possible: GG, GT or TT.
(EXPLANATION TO TABLE BELOW)

| The probability of developing a MI if the genotype is GG | | P(MI)GG) | 21% |
|---|---|---|---|
| P(MI \| GG) | 21% | P(MI \| nonGG) | 18% |
| P(Healthy \| nonGG) | 82% | P(Healthy \| GG) | 79% |
| P(MI \| GT) | 14% | P(MI \| nonGT) | 24% |
| P(Healthy \| nonGT) | 76% | P(Healthy \| GT) | 86% |
| P(MI \| TT) | 53% | P(MI \| nonTT) | 18% |
| P(Healthy \| nonTT) | 82% | P(Healthy \| TT) | 47% |

As can be seen in the results set forth in Table 3 above, the different genotypes have a large impact on the probability for developing disease where the genotype TT has, by far, the largest effect. The risk of developing a myocardial infarction is 53% with the TT genotype and 47% to stay healthy with the same genotype. The probability is 82% to stay healthy if the subject has a different (GG or GT) genotype in that specific position.

Thus, using the teachings of the present invention, it is possible to identify individuals that are at an increased risk for developing a myocardial infarction independent of the levels of cholesterol in the blood (where low levels of cholesterol is usually considered a protective factor).

What is claimed is:

1. An isolated nucleic acid comprising the sequence set forth in SEQ. ID NO: 1, wherein said sequence comprises nucleotides selected from the group consisting of: a T residue at position 92; a G residue at position 175; a T residue at position 185; a G residue at position 197; and combinations of the foregoing residues at said positions.

2. An isolated nucleic acid as defined in claim 1, wherein said nucleic acid is DNA.

3. An isolated nucleic acid as defined in claim 1, wherein said nucleic acid is RNA.

4. A recombinant DNA vector comprising a nucleic acid as defined in claim 1.

5. A probe which hybridizes under high stringency conditions to the sequence set forth in SEQ ID NO: 1.

6. A library of nucleic acids, each of which comprises one or more polymorphic positions within the promoter sequence of human MTP gene, wherein said polymorphic positions are selected from the group consisting of positions in the MTP promoter region numbered 92, 175, 185 and 197.

7. An isolated nucleic acid comprising 10 to 100 base pairs from the human gene encoding MTP, wherein said nucleic acid comprises a polymorphic position selected from the group consisting of a position in the promoter region numbered 92, 175, 185 and 197 in SEQ ID NO: 1.

* * * * *

SEQUENCE LISTING

<160> NUMBER OF SEQ ID NOS: 12

<210> SEQ ID NO 1
<211> LENGTH: 209
<212> TYPE: DNA

<213> ORGANISM: Human

<400> SEQUENCE: 1

| gctccaacct catacagttt cacacataag gacaatcatc tatgtttcat gaaagttcta | 60 |
| tctactttaa cattattttg aagtgattgg tggtggtatg aattaacagt ttaaatttaa | 120 |
| atcctaaaat tcagtgtgaa tttttataa tagcataaaa attcaaagat gtccatacaa | 180 |
| gaaaaattaa aatttggtta ggtttagca | 209 |

<210> SEQ ID NO 2
<211> LENGTH: 23
<212> TYPE: DNA
<213> ORGANISM: Human

<400> SEQUENCE: 2

| ccctcttaat ctctttccta gaa | 23 |

<210> SEQ ID NO 3
<211> LENGTH: 21
<212> TYPE: DNA
<213> ORGANISM: Human

<400> SEQUENCE: 3

| aagaatcatt gaccagcaat c | 21 |

<210> SEQ ID NO 4
<211> LENGTH: 20
<212> TYPE: DNA
<213> ORGANISM: Human

<400> SEQUENCE: 4

| ccagctagga gtcactgaga | 20 |

<210> SEQ ID NO 5
<211> LENGTH: 23
<212> TYPE: DNA
<213> ORGANISM: Human

<400> SEQUENCE: 5

| tagaaatgag attcagaaag gac | 23 |

<210> SEQ ID NO 6
<211> LENGTH: 21
<212> TYPE: DNA
<213> ORGANISM: Human

<400> SEQUENCE: 6

| caatcatcta tgtttcatca a | 21 |

<210> SEQ ID NO 7
<211> LENGTH: 18
<212> TYPE: DNA
<213> ORGANISM: Human

<400> SEQUENCE: 7

| aagtttcctc atgggtga | 18 |

<210> SEQ ID NO 8
<211> LENGTH: 32
<212> TYPE: DNA
<213> ORGANISM: Human

<400> SEQUENCE: 8

```
ggatttaaat ttaaactgtt aattcatatc ac                                32
```

<210> SEQ ID NO 9
<211> LENGTH: 27
<212> TYPE: DNA
<213> ORGANISM: Human

<400> SEQUENCE: 9

```
agtttcacac ataaggacaa tcatcta                                      27
```

<210> SEQ ID NO 10
<211> LENGTH: 52
<212> TYPE: DNA
<213> ORGANISM: Human

<400> SEQUENCE: 10

```
agtcacgacg ttgtaaaacg acggccagta cataaggaca atcatctatg tt          52
```

<210> SEQ ID NO 11
<211> LENGTH: 21
<212> TYPE: DNA
<213> ORGANISM: Human

<400> SEQUENCE: 11

```
tcttgtatgg acatctttga a                                            21
```

<210> SEQ ID NO 12
<211> LENGTH: 24
<212> TYPE: DNA
<213> ORGANISM: Human

<400> SEQUENCE: 12

```
cgacgttgta aaacgacggc cagt                                         24
```